June 8, 1965 J. G. DU PUIS, JR Plant Pat. 2,528
AVOCADO TREE
Filed April 13, 1964
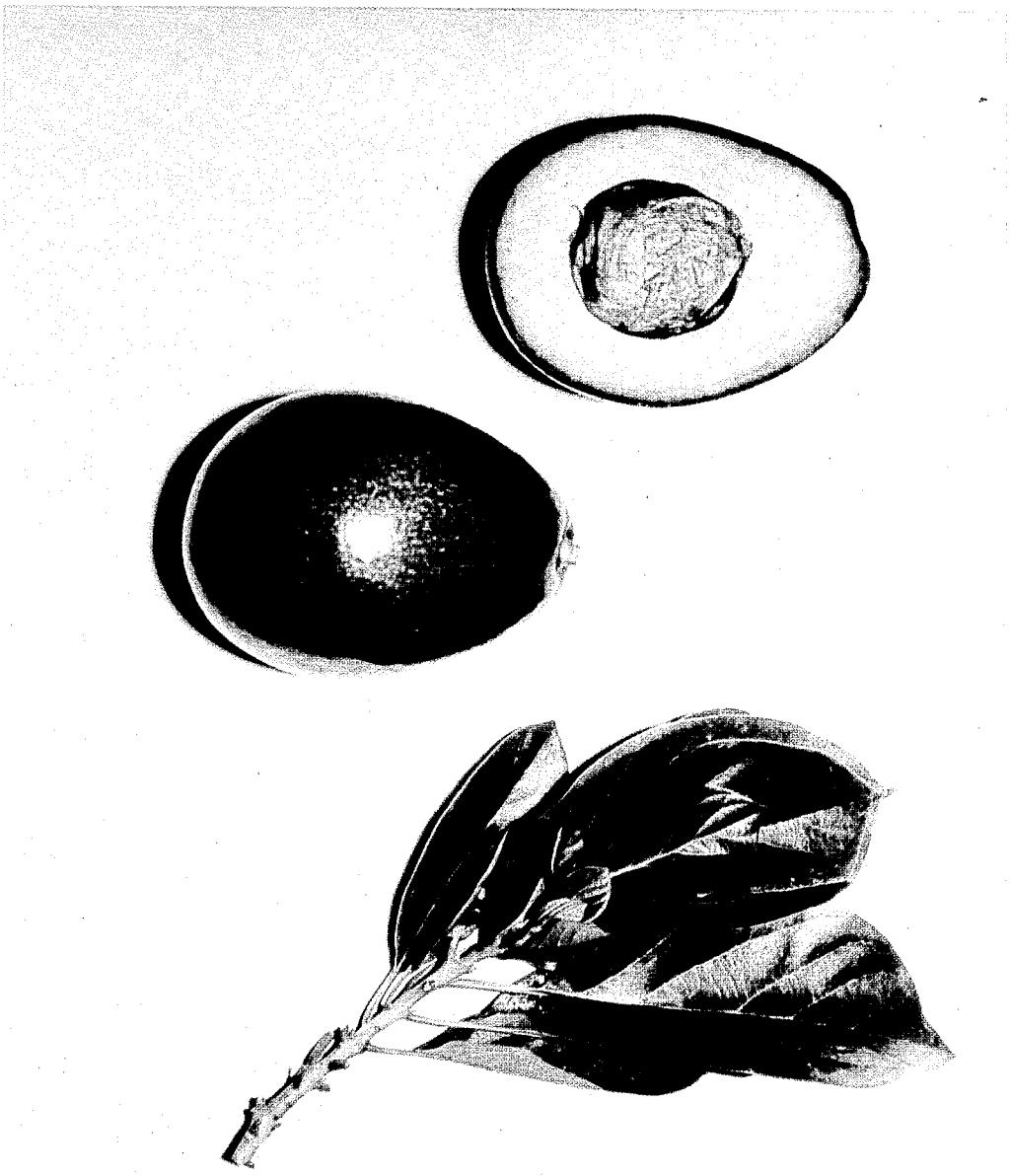
John G. Du Puis Jr United States Patent Office Plant Pat. 2,528
Patented June 8, 1965

2,528
AVOCADO TREE

John G. Du Puis, Jr., 6000 NW. 32nd Ave., Miami, Fla.

Filed Apr. 13, 1964, Ser. No. 359,534
1 Claim. (Cl. Plt.—44)

This invention pertains to a new and distinct variety of avocado tree, which tree has certain highly desirable characteristics. In June and July during the early part of the avocado season in Florida, the market desires an attractive, smooth-skinned, small avocado fruit with a relatively small seed, rather tight in its seed cavity, with a bright yellow flesh and the quality of shipping a long distance to market. The flesh quality must be high to compete with off-shore fruit. From the viewpoint of the grower, trees should not be too spreading and should be relatively upright in growth to alleviate crowding in the grove and allow for adequate cultivation. Trees should have vigorous growth and be fairly resistant to most avocado diseases. Blooming should be early to help ensure earlier maturity and the trees should have the ability to set heavy, well distributed crops of fruit each year.

The tree of my new variety answers all of the general specifications listed above, plus others. Buds and grafts of this tree on different rootstocks produced young plants of excellent vigor and several larger trees that were topworked with graftwood from this variety also showed outstanding vigor, and have produced fine crops of uniform fruit each year.

This new variety originated in my grove at Miami, Florida, as a limb mutation from a selective seedling whose parentage is unknown, but probably of West Indian origin. This new variety was far superior to the original parent tree and the high quality of the fruit was quite apparent after several years of observation. This variety has been asexually reproduced by budding and grafting in my grove in Miami, without apparent variation from the original stock.

Accompanying illustrations show in approximately true colors, a specimen of the fruit, a cross-section of another specimen, and a small twig with both juvenlie and mature leaves.

This new variety of avocado tree to which this invention is directed is a tree of upright to slightly spreading growth.

The foliage of this tree is quite distinctive in that the leaves are broadly obovate, elongating slightly as they mature, opening flat and well spaced on the twigs. The leaf tip is sub-acuminate and the leaf base is cuneate. The leaf margins are entire with slight undulations. The main venation on the upper surface of the leaves is much lighter in color than the lamina, presenting a distinct contrast.

Young leaves are copper colored to bronze (Maerz and Paul, Dictionary of Color, Plate 14, A–B–C–D, 8–9–10) with veining of a yellow-green (Plate 20, J–K–L, 2–3). Underside of the leaves is duller, but in the same color range.

Mature leaves are glossy to semi-glossy on the upper surface (Plate 23, E–H–J, 7–8–9). Undersides are a dull shade of light green (Plate 21, C–D–E, 5–6). The stems are a yellow green (Plate 20, J–K–L, 3–4).

Blooming takes place in very early spring (February) and the perfect flowers appear both as terminal and axillary clusters.

This new variety of avocado has the ability to set and hold a well distributed crop of young fruits, making it a more desirable commercial crop. The fruit matures from the middle of June to the end of July.

The fruit is oblong to pyriform with a smooth, green skin (Plate 20, K–L, 8–9–10) with a fair scattering of light yellow stomata which does not contrast greatly with the ground color. The short stem is firmly attached both to fruit and branchlet. Fruits vary in weight from 10 to 16 ounces, most averaging about 12 ounces. Length varies from 4½ to 5 inches, and breadth varies from 3 to 3½ inches. The seed is small for this size of fruit, almost round in shape, fitting tightly in the seed cavity, and covered with a light brown closely adhering covering. The flesh of the fruit is very firm, free of fibre, and of a rich nutty flavor. The color is a very attractive light yellow (Plate 17, I–J–K, 1) shading to a light green at the cortex (Plate 18, J–K, 7–8) just next to the skin.

The distinguishing characteristics of the tree of this invention are the distinctive appearance of the fruit with its high market quality, outstanding flavor, and relatively small seed; the ability to set and hold fruit even during adverse weather conditions; symmetrical, semi-upright growth; and its resistance to avocado scab. Its early season maturity and dependable production year after year are also important. The growth habits might vary during different seasons or perhaps in different localities, but the description as here given is true. This tree could definitely be recommended for planting in the lower east coast regions of Florida, as well as the off-shore islands to the east and south.

Having thus disclosed my invention, I claim:

The new and distinct variety of avocado tree, substantially as herein shown and described, characterized particularly by its moderately upright, compact growth, symmetrical with evenly distributed branches; its leaves broadly obovate; a flowering period occurring very early in the spring (February); its fruit maturing season each year from mid June to the end of July; ability to set and hold fruit under adverse weather conditions; the fruit being further characterized as oblong with a smooth green skin with scattered light yellow stomata, seed that is relatively small, and flesh that is firm, free from fibre, and of an exceptionally rich nutty flavor.

No references cited.

ABRAHAM G. STONE, *Primary Examiner.*